(12) United States Patent
Lee

(10) Patent No.: US 6,454,732 B1
(45) Date of Patent: Sep. 24, 2002

(54) APPARATUS FOR RISING AND FALLING MEDICATOR OF AUTOMATIC HOT-HEAT TREATMENT DEVICE

(75) Inventor: Sang-bok Lee, Taejon (KR)

(73) Assignee: Migun Medical Instrument Co., Ltd., Chungcheongham-do (KR)

(*) Notice: Subject to any disclaimer, the term of this patent is extended or adjusted under 35 U.S.C. 154(b) by 0 days.

(21) Appl. No.: 09/722,680

(22) Filed: Nov. 28, 2000

(30) Foreign Application Priority Data

Dec. 3, 1999 (KR) .............................. 99-54664

(51) Int. Cl.$^7$ ................................. A61H 7/00
(52) U.S. Cl. .................... 601/101; 601/103; 601/98; 601/15; 601/18
(58) Field of Search ............... 601/97, 98, 99, 601/100, 101, 103, 15, 18, 19

(56) References Cited

U.S. PATENT DOCUMENTS 6,056,707 A * 5/2000 Hayashi ................... 601/103
6,290,660 B1 * 9/2001 Epps et al. ................. 601/41

OTHER PUBLICATIONS

Translation of the decision dated May 26, 2000 (Statements of Relevance) in common with Korean Registered Utility Model No. Silyong–0182021–00–00.

* cited by examiner

Primary Examiner—Michael A. Brown
Assistant Examiner—Benjamin K. Koo
(74) Attorney, Agent, or Firm—Rothwell, Figg, Ernst & Manbeck

(57) ABSTRACT

An apparatus for rising and falling a medicator of an automatic hot-heat treatment device, includes: a movement space formed vertical to a main body of a movable body horizontally moving along with a screw rotated by a motor; a treatment device moving plate having a carrying bar insertedly bound with the movement space and moving in the movement space its horizontal movement and a jaw at the lower end portion of the carrying bar; and a rising and falling spring positioned between the treatment device moving plate and the movable body, for moving the madicator up and down so as to be tensed and contracted according to the curve of the body of the user to thereby pressurize and foment the diseased part of the user.

7 Claims, 4 Drawing Sheets

APPARATUS FOR RISING AND FALLING MEDICATOR OF AUTOMATIC HOT-HEAT TREATMENT DEVICE

BACKGROUND OF THE INVENTION

1. Field of the Invention

The present invention relates to an apparatus for rising and falling a medicator of an automatic hot-heat treatment device, and more particularly to an apparatus for rising and falling a medicator of an automatic hot-heat treatment device in which a rising and falling spring is formed between a movable body horizontally moving along a screw and a treatment device moving plate and the treatment device moving plate is moved up and down by virtue of the rising and falling spring, so that the medicator is closely adhered on the curve of the body of a user, pressurizing and fomenting a diseased part of the body with equal force.

2. Description of the Background Art

Generally, widely used physical treatment devices for home use or installed in specific clinics largely include a hot-heat treatment device which is designed to pressurize and foment the diseased part of a user by using a Helium lamp or an infrared lamp, and a radio frequency treatment device using a radio frequency lamp.

In case where a user desires to use the treatment devices (the hot-heat treatment device and the radio frequency treatment device), the treatment device is supposed to be accurately positioned on a spot on the body suitable for acupuncture of the joint of the backbone of the user and moved to the next joint of the backbone as certain time elapses.

However, as for this treatment, after the user puts the treatment device on the backbone with his or her hands, he or she should move it to the next backbone joint in the same manner, which, thus, is inconvenient for a patient who has a problem to move. In spite of the trouble, if the user intends to use the treatment device, he or she would have difficulty in accurately positioning it on the spot on the body suitable for acupuncture of the joint of the backbone, which is not effective for hot-heat treatment.

Therefore, recently, in an effort to overcome the shortcomings, there has been proposed a mat for hot-heat treatment capable of automatically pressurizing and fomenting the spot on the body suitable for acupuncture of the joints of the backbone of the user.

FIG. 1 is a plan view of a general hot-heat treatment mat. FIG. 2 is a side-sectional view of the general hot-heat treatment mat. FIG. 3 is a front view of the general hot-heat treatment mat.

As shown in the drawing, the hot-heat treatment mat includes a main body 100 in a mat type on which the user is to lie down; a reciprocal motor 200 fixed installed at a portion of the main body 100; a screw 300 idly rotated upon receipt of driving force by a belt 210 as the reciprocal motor 200 is driven; a movable body 500 for being threaded with the screw 300 and being reciprocally moved forwardly and backwardly as the screw 300 is idly rotated, the movable body having a space in a vertical direction; a treatment device moving plate 400 having a moving bar 420 at its lower portion to be inserted in the space 510 and movement rails 410 at its right and left sides, on which the hot-heat treatment device is fixedly mounted; and an indented rail 600 having an indented surface 610 on which the treatment device moving plate 400 and the hot-heat treatment device are concurrently moved upwardly and downwardly.

In order to use the mat for hot-heat treatment, first, the medicator is fixedly mounted on the upper surface of the treatment device moving plate 400. And then, in a state that the user lies down on the main body 100, when electric power is applied to the reciprocal motor 200, the driving force of the reciprocal motor 200 is transferred to the screw 300 and the screw 300 is idly rotated in the direction in which the reciprocal motor 200 is driven.

Then, the movable body 500 is linearly and reciprocally moved along the screw 300. At this time, the treatment device moving plate 400 is linearly and reciprocally moved on the indented rail 600 along with the movable body 500 by the moving bar 420, and when the movement rail 410 is guided along the indented surface 610, the moving bar 420 is moved freely, so that the treatment device moving plate 400 and the hot-heat treatment device can be moved upwardly and downwardly, thereby pressurizing and fomenting the joints of the backbone of the user.

As described above, the general mat for hot-heat treatment is effective in the aspect that the spots on the body suitable for acupuncture of the joints of the backbone of the user can be automatically pressurized and fomented with the automatic hot-heat treatment device moved.

However, in order for the medicator to be closely adhered on the curve of the body while the medicator is moved up and down, an additional indented rail 600 having the indented surface 610 must be installed.

In addition, since the medicator is moved up and down along the pre-set indented surface 610, the force for pressurization (acupressure) is unevenly applied, resulting in that there may cause a pain during treatment and thus an effective pressurizing and fomenting treatment is hardly expected.

SUMMARY OF THE INVENTION

Therefore, an object of the present invention is to provide an apparatus for rising and falling a medicator of an automatic hot-heat treatment device in which a rising and falling spring is formed between a movable body horizontally moving along a screw and a treatment device moving plate and the treatment device moving plate is moved up and down by the rising and falling spring, so that the medicator is closely adhered on the curve of the body of a user, pressurizing and fomenting a diseased part of the body with equal force.

To achieve these and other advantages and in accordance with the purpose of the present invention, as embodied and broadly described herein, there is provided an apparatus for rising and falling a medicator of an automatic hot-heat treatment device, including: a movement space formed vertical to a main body of a movable body horizontally moving along with a screw rotated by a motor; a treatment device moving plate having a carrying bar insertedly bound with the movement space and moving in the movement space its horizontal movement and a jaw at the lower end portion of the carrying bar; and a rising and falling spring positioned between the treatment device moving plate and the movable body, for moving the madicator up and down so as to be tensed and contracted according to the curve of the body of the user to thereby pressurize and foment the diseased part of the user.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
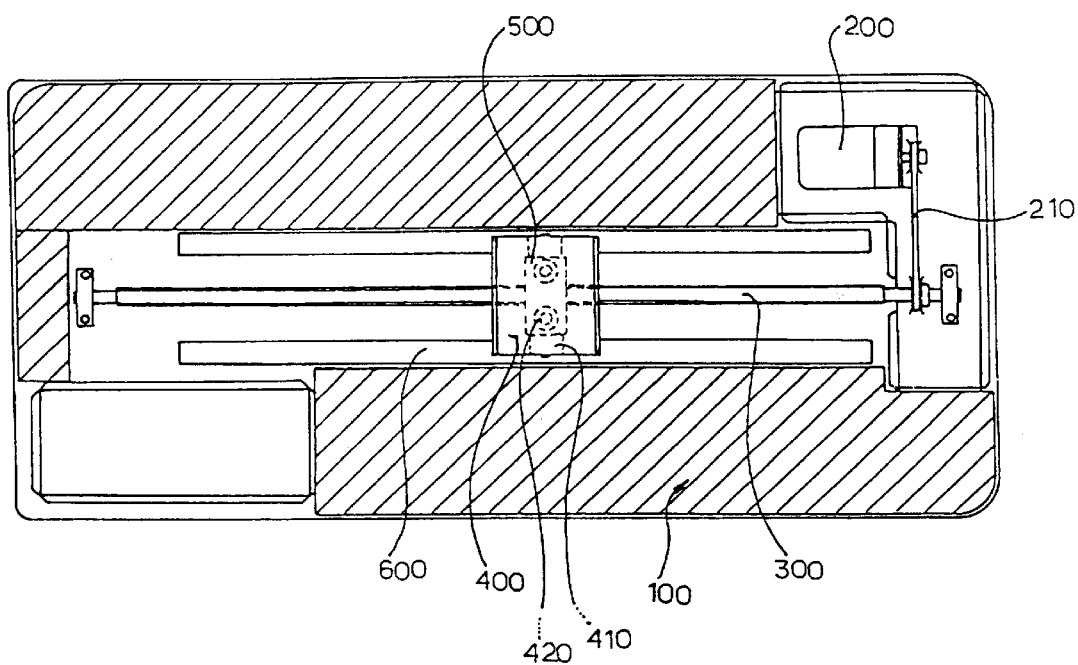
FIG. 1 is a plan view of a general mat for hot-heat treatment.
Figure 2:
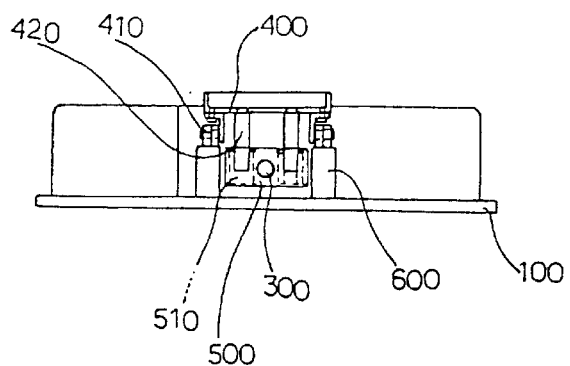
FIG. 2 is a vertical-sectional view of the general mat for hot-heat treatment.
Figure 3:
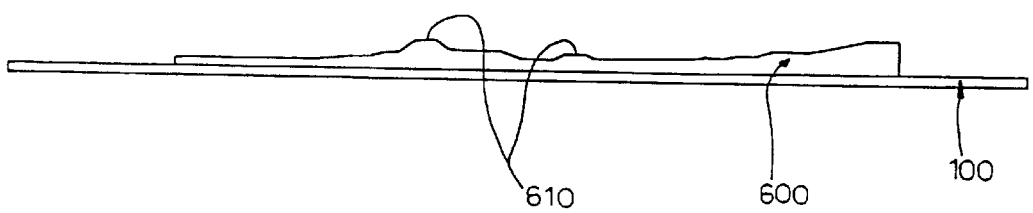
FIG. 3 is a front view of the general mat for hot-heat treatment.
Figure 4:
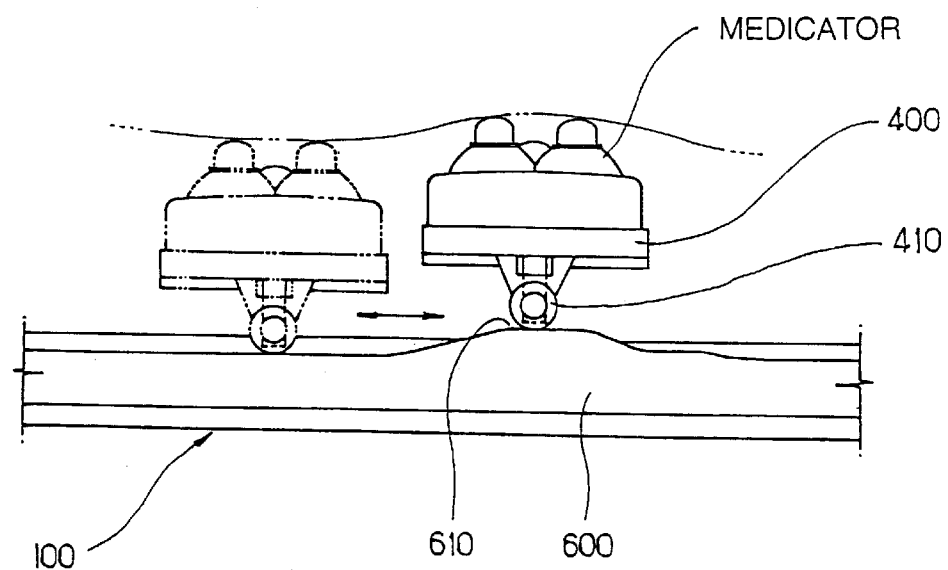
FIG. 4 is a view showing a major part of the general mat for hot-heat treatment in accordance with the present invention.

Reference will now be made in detail to the preferred embodiments of the present invention, examples of which are illustrated in the accompanying drawings.

The mat for hot-heat treatment of the present invention has the same mat-type as that of the conventional art.

That is, the hot-heat treatment of the present invention basically includes a main body 100 in a mat type on which the user is to lie down; a reciprocal motor 200 fixed installed at a portion of the main body 100; a screw 300 idly rotated upon receipt of a driving force by a belt 210 as the reciprocal motor 200 is driven; a movable body 500 for being threaded with the screw 300 and being reciprocally moved forwardly and backwardly as the screw 300 is idly rotated, the movable body having a space in a vertical direction; a treatment device moving plate 400 having a moving bar 420 at its lower portion to be inserted in the space 510 and movement rails 410 at its right and left sides, on which the hot-heat treatment device is fixedly mounted; and an indented rail 600 having an indented surface 610 on which the treatment device moving plate 400 and the hot-heat treatment device are concurrently moved upwardly and downwardly.

Figure 5:
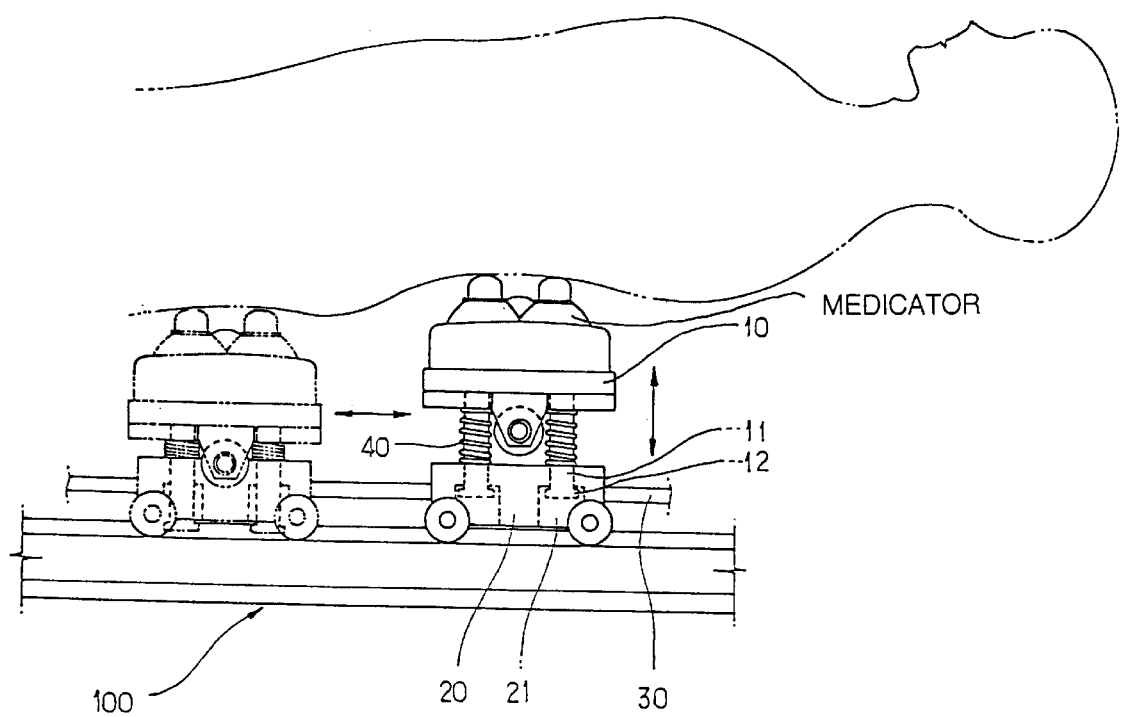
FIG. 5 shows a state that the rising and falling apparatus is installed and used in accordance with the present invention.

However, as shown in FIG. 5, in order to have more effective treatment, the mat for hot-heat treatment of the present invention further includes a movement space 21 formed vertical to a main body of a movable body 20 horizontally moving along with a screw 30 rotated by a motor; a treatment device moving plate 10 having a carrying bar 11 insertedly bound with the movement space 21 and moving in the movement space 21 its horizontal movement and a jaw 12 at the lower end portion of the carrying bar 11; and a rising and falling spring 40 positioned between the treatment device moving plate 10 and the movable body 20, for moving the madicator up and down so as to be tensed and contracted according to the curve of the body of the user to thereby pressurize and foment the diseased part of the user.

The operation of the apparatus for rising and falling a medicator of an automatic hot-heat treatment device of the present invention constructed as described above will now be explained.

First, the medicator is fixedly mounted on the treatment device moving plate 10. In a state that the user lies down on the main body 100, when the hot-heat treatment device is operated, the screw 30 is idly rotated by a motor, and the movable body 20 and the treatment device moving plate 10 is horizontally moved along the screw 30.

At this time, since the rising and falling spring 40 is stretched and contracted according to the body curve of the user, the treatment device moving plate 10 is moved up and down along with the medicator when it is horizontally moved together with the movable body 20, and thus, the medicator is closely adhered on the body of the user, pressurizing and fomenting the diseased part of the user with the consistently uniform force.

And, since the jaw of the carrying bar is caught in the movement space, the treatment device moving plate won't release in spite of the spring force of the rising and falling spring.

As so far described, according to the automatic hot-heat treatment device, and more particularly to an apparatus for rising and falling a medicator of an automatic hot-heat treatment device of the present invention, since the rising and falling spring is formed between the movable body and the treatment device moving plate, when they are horizontally moved, the treatment device moving plate is moved up and down by virtue of the rising and falling spring. Accordingly, the medicator is closely adhered on the body curve of the user, pressurizing and fomenting the diseased part of the user with the consistently uniform force.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. An automatic hot-heat treatment apparatus, comprising:
    a movable body moving in a horizontal direction along a screw rotated by a motor;
    a movement space located inside the movable body;
    a treatment moving plate having a carrying bar extending through and movable within the movement space in a vertical direction, and a jaw disposed at the lower end portion of the carrying bar for retaining the treatment moving plate within the movement space;
    a medicator affixed to the treatment moving plate; and
    a spring positioned between the treatment moving plate and the movable body for moving the medicator in the vertical direction,
    wherein the medicator expands and contracts according to the curvature of a body of a user to thereby uniformally treat a diseased part of the user.

2. The treatment apparatus of claim 1, wherein the diseased part of the user is treated by pressure and fomentation.

3. The treatment apparatus of claim 1, wherein a width of the movement space is smaller than a width of the jaw.

4. The treatment apparatus of claim 1, wherein a width of the movement space is larger than a width of the carrying bar.

5. The treatment apparatus of claim 1, wherein a width of the jaw is larger than a width of the carrying bar.

6. The treatment apparatus of claim 1, wherein the horizontal direction is left to right or right to left.

7. The treatment apparatus of claim 1, wherein the vertical direction is up and down.

* * * * *